United States Patent [19]

Gheysens et al.

[11] Patent Number: 6,017,371
[45] Date of Patent: Jan. 25, 2000

[54] COMPOSITION AND METHOD FOR PRODUCING A MULTIPLE BOILING POINT ETHER GASOLINE COMPONENT

[75] Inventors: Jean-Louis G. Gheysens, San Ramon, Calif.; William J. Wells, III, Carrollton, Tex.; Richard E. Woodling, Los Gatos, Calif.

[73] Assignee: NRG Technologies, Inc., San Francisco, Calif.

[21] Appl. No.: 08/102,708

[22] Filed: Aug. 5, 1993

Related U.S. Application Data

[63] Continuation of application No. 07/832,745, Feb. 7, 1992, abandoned.

[51] Int. Cl.[7] .................................................. C10L 1/18
[52] U.S. Cl. ........................... 44/448; 568/671; 568/697
[58] Field of Search ........................... 44/447, 448, 449; 568/698, 671

[56] References Cited

U.S. PATENT DOCUMENTS

| | | | |
|---|---|---|---|
| 2,046,243 | 6/1936 | Buc | 44/449 |
| 2,480,940 | 9/1949 | Leum . | |
| 2,952,612 | 9/1960 | Trainer | 44/449 |
| 3,224,848 | 12/1965 | Henderson | 44/449 |
| 4,193,770 | 3/1980 | Chase et al. | 44/449 |
| 4,361,422 | 11/1982 | Derrien et al. | 44/449 |
| 4,468,233 | 8/1984 | Bruderreck et al. | 44/449 |
| 4,519,809 | 5/1985 | Hochhauser | 44/449 |
| 5,001,292 | 3/1991 | Harandi et al. | 585/322 |
| 5,070,016 | 12/1991 | Hallberg | 435/132 |

FOREIGN PATENT DOCUMENTS

| | | | |
|---|---|---|---|
| 0504470 | 4/1939 | United Kingdom | 44/449 |

OTHER PUBLICATIONS

USPTO Disclosure Document: Mixed Alcohols and Mixed Tertiary–Butyl–Ethers as High Performance–Low Polluting Fuels in Internal Combustion Engines, dated Nov. 14, 1988.

*Primary Examiner*—Margaret Medley
*Attorney, Agent, or Firm*—Limbach & Limbach LLP

[57] ABSTRACT

A composition and method for producing a multiple boiling point ether gasoline component is provided. A mixed alcohol composition including predominantly $C_1$–$C_3$ alcohols is reacted with an alkene stream to produce a mixture of ethers having different boiling points. The ether mixture is useful, when blended with gasoline, to increase oxygenation and overall motor fuel performance.

9 Claims, 4 Drawing Sheets

COMPOSITION AND METHOD FOR PRODUCING A MULTIPLE BOILING POINT ETHER GASOLINE COMPONENT

This is a continuation of application Ser. No. 07/832,745 filed on Feb. 7, 1992 now abandoned.

FIELD OF THE INVENTION

The invention relates to a motor fuel component having relatively high oxygen content and especially beneficial blending characteristics. The invention also involves an efficient, integrated method for producing the composition.

BACKGROUND OF THE INVENTION

Since the early 1970's extensive research has been performed to increase the efficiency of use of crude oil through quantitative and qualitative improvements of fossil fuels and related feedstocks, petrochemical products and alternative fuels. A primary motivation for this research has been to ensure that the phasing-out of lead alkyl in gasoline would not adversely affect the gasoline pool and the octane pool. While the increase in gasoline prices during the 1970's motivated investors and researchers to develop alternative energy sources, the drop in oil prices in recent years has caused a virtual cessation of investment in alternative fuels.

Today, the passage of the Clean Air Act (CAA) amendments of 1990 is leading to landmark changes in all major transportation fuels in the United States, and a substantial promotion of alternative motor fuels, mainly so-called "oxygenates." In order to comply with the CAA, gasoline marketers are not only admixing oxygenates into gasoline, but also changing the hydrocarbon composition, for example, benzene content, total aromatics, butane content, total olefins, etc. It is these considerations and others that will determine the reactivity of new gasolines and which will translate into the performance characteristics of admixed oxygenates, i.e., distillation, volatility, azeotropic behavior, oxidation stability, solubility, octane values, vapor pressure, etc.

Over the last fifteen years research regarding oxygenated fuel substitutes and components have focused on certain alcohols and ethers, mainly methanol, ethanol, isopropanol, t-butanol, methyl t-butyl ether (MTBE), ethyl t-butyl ether (ETBE), and t-amyl methyl ether (TAME). Many processes and compositions of such materials have been described in the art.

For example, U.S. Pat. No. 5,001,292 to Harandi et al, describes a process for reducing the cost of producing MTBE and other alkyl t-butyl ethers by converting unreacted hydrocarbons and alkanols from the etherification process to gasoline boiling range hydrocarbons.

Generally, oxygenate gasoline components have been blended into gasoline separately. However, there have been mixtures of such components disclosed, such as blends of gasoline containing components other than ethers, such as alcohols, and even esters. For example, U.S. Pat. No. 4,468,233 to Bruderreck et al. describes a t-butyl ether containing motor fuel composition including MTBE and isopropyl t-butyl ether (i-PTBE) and sec-butyl t-butyl ether (s-BTBE) which is said to provide a high octane number, reduced emissions and improved solubility. However, some experiments contradict the finding that ether blends improve alcohol solubility in gasoline.

Gasoline has historically pressures of 10–15 psi. Ether components have provided advantageous vapor pressure blending characteristics for such gasolines. The CAA has now caused refiners to reformulate gasoline to achieve vapor pressures of 7.5 to 8.5 psi with such lower vapor pressures the motivation to use MTBE, the strongest oxygenate gasoline component in the marketplace, becomes weakened because MTBE has a vapor pressure of approximately 8.4 psi.

The future use of more highly oxygenated fuels will inevitably be tied to environmental improvement efforts, but the blending of MTBE and ethanol with gasoline for octane improvement or supply extension with improved profitability will also continue. Even areas presently unaffected by carbon monoxide or ozone loss will probably be required to use oxygenates by 1995 or earlier because of anti-dumping provisions in the CAA. The need for more oxygenates is clear. Hence, more feedstocks and technologies must be developed to supply the market demand.

The CAA deals not only with mobile emissions, but also static emissions, which are of concern to the oil industry. RCRA hazardous waste management rules affecting refiners will provide new incentives for research related to more efficient conversion of heavy crudes, still bottoms and residues, all generally referred to as the "bottom of the barrel". Other energy related and overall environmental concerns will be addressed in this research as well, such as use and conversion of oil shale, use of coal and lignite, the recovery of industrial and urban waste, etc.

Several technologies and processes exist that, operating in liquid phase for methanol and gaseous phase for mixed alcohols production can, either connected, or operated independently, provide new opportunities for fuel alcohol synthesis. Their flexibility enables them to be used either with the products of gasification derived from, for example, coal, lignite, heavy residues, biomass, urban and industrial wastes, or with synthesis gas (Syn-Gas) produced by partial oxidation and/or steam reforming of natural gas or light napthas, or even heavy oils and crudes, crude oil bottoms and residues.

Such processes can be used to produce a linear combination of alcohols composed of at least 30 to 40% longer alcohol chains.

SUMMARY OF THE INVENTION

It is thus an object of the present invention to identify an oxygenated fuel substitute or blending agent which allows compliance with CAA requirements.

It is a further object of the invention to provide a method of less expensively producing such oxygenated compositions so that refiners will be economically motivated to produce such compositions in greater quantities.

It is yet a further object of the invention to provide a method which uses as a feed stock, refinery still bottoms and other refinery streams which are difficult or expensive to handle, as well as lower cost hydrocarbon sources such as coal, lignite, oil shale and even relatively low calorie content industrial and urban wastes.

Finally, it is an object of the invention to identify compositions which may be blended with gasoline without adversely affecting the performance characteristics of the final product, such that the blend is immediately useful in automobile engines.

In order to meet these objects, the present invention provides a composition of mixed ethers having multiple boiling points so that when mixed with gasoline, octane is increased while distillation characteristics remain substantially similar to the unmixed gasoline. The mixed ether gasoline component preferably includes at least $C_1$ to $C_4$ tert-butyl or tert-amyl ethers, which composition provides especially advantageous blending characteristics with motor fuels.

The method of the invention comprises etherifying a thermochemical alkanol mixture of at least $C_1$–$C_4$ alcohols with alkenes to produce the mixed ether composition of the invention. The alkanol mixture can be synthesized from refinery streams such as still bottoms, which normally require substantial amounts of processing to achieve a valuable product, or which must be disposed of as hazardous waste. The method eliminates major equipment needs and operating costs associated with purchasing, storage of intermediates, waste management and refinery compliance with the CAA and other applicable regulations.

BRIEF DESCRIPTION OF THE DRAWINGS

The invention will be better understood by reference to the attached figures of which.

DETAILED DESCRIPTION OF THE PREFERRED EMBODIMENTS

The present invention substantially overcomes the above noted problems and disadvantages by use of a process for making mixed boiling point alkyl t-alkyl and/or aryl t-alkyl ether products such that improved, gasoline compositions are formed. The process produces a mixed multiple boiling point ether which may also include multiple boiling point alcohols in the aforementioned fuels.

The process developed by this invention eliminates major equipment needs and operating costs associated with purchasing, maintenance, waste management, hazards, productivity and refinery compliance renovations as enacted by the CAA for as early as 1992 and becoming more stringent beginning in 1995.

The integrated processing method of the present invention combines the recovery of refinery residues and steam reforming of light napthas in order to provide the refiner with the ability to become self sufficient in etherification feedstocks so as to allow compliance with CAA requirements for the production of at least 2.0 to 3.1 or more percent oxygen containing gasoline. By employing the method of the present invention, in addition to providing etherification from FCC butenes and optional butanes, the refiner can upgrade refinery products by use of lower quality crude oil and poorer quality atmospheric residues (off-gases). At the same time, the refinery eliminates a potential feedstock loss, and a potentially hazardous waste is efficiently used.

In order to produce a multiple boiling point ether gasoline component of the present invention a mixed alcohol is reacted with a stream of alkenes, preferably olefins or dienes. The mixed alcohol component can be produced by Fisher-Trophs synthesis or via Syn-Gas techniques from hydrocarbon sources such as natural gas, light napthas or even crude oil bottoms and residues, thereby providing the refiner with additional benefits.

Thus, in the present invention, purchase of linear alcohols and their stockpiling becomes unnecessary. By choosing the proper catalysts (examples: alkali promoted zinc-chrome based, copper-cobalt based, copper-zinc based, molybdenum-cobalt-potassium) to obtain a preferred selectivity, the desired linear alcohol mixture is produced.

A first typical multiple boiling point alcohol product that usually contains about 70% methanol with about 30% higher ($C_{2+}$) alcohols is hereafter referred to as "thermochemical methanol".

Another typical multiple boiling point alcohol comprises as its major components ethanol and isopropanol and is hereafter designated "thermochemical ethanol". It should be understood, however, that other catalytically produced or mixed alcohol are useful in the present invention. In most cases these mixed boiling point alcohols, when purified, will preferably not contain more than 0.1% water, though higher levels may be acceptable and even favorable for use in the present invention.

It is yet another advantage of the invention that water (normally very undesirable) in the alcohol will be "self-correcting" as part of the etherification process, in that residual water acts as a washer and extractor of the unconverted lower molecular weight alcohols that would otherwise stay in the organic phase and be detrimental to vapor pressure blending performance of the product ethers in the gasoline blend.

For this reason, processes for the production of thermochemical alcohols which utilize expensive and sometimes contaminating inorganic catalysts to produce very low water content product need not be used. To the contrary alcohol mixtures containing relatively large amounts of water are useful in the present invention. Specifically, water content can be greater than 0.1% v/v without any detrimental effect.

Moreover, higher boiling alcohol chains can be tailored to specific end uses using larger molecules such as $C_8$–$C_{16}$, and preferably $C_8$–$C_{12}$, as well as other alcohols such as polyhydric alcohols and polyols.

Finally, the integrated process of the invention now enables, without a need for additional cosolvents, the processing of a substantially water free alcohol stream with a distillation curve of about 55 to about 200 degrees centigrade into a single etherification path, converting every cut and azeotrope by reaction with selected or combined olefins and/or dienes (preferably using $C_3$ to $C_6$) to ethers with yields of about 60 to about 95% or higher.

While greater efficiency is achieved in the process of the invention, the obtained multiple boiling point ether (MBPE), when mixed with gasoline, provides surprisingly even and consistent distribution of oxygen throughout the distillation curve, thereby yielding similar, although improved driveability characteristics compared to neat gasoline.

As shown by examples below, one measure of the performance of a given fuel blend is the so-called "D-86" curve. The D-86 curve is generated by a standard procedure (ASTM D-86) known in the field for characterizing the distillation profile of motor fuels.

The typical feedstock material for the present invention consists of the traditional etherification components such as the olefinic streams of FCC light cracked gas containing butene isomers often in mixture with substantial amounts of propene, propane, n-butane and isobutane. The $C_4$ components usually contain a major amount of unsaturated compounds, such as 10–25% isobutylene, 25–55% linear butenes, and small amounts of butadiene.

Also, $C_{4+}$ heavier olefinic hydrocarbon may be used, particularly isobutylene and/or isoamylene. These aliphatic streams are produced in a variety of petroleum refinery operations such as catalytic cracking operations.

If desired, dienes such as isoprene and methylcyclopentadiene can be used as a replacement for $C_{4+}$ olefins.

The alcohol feedstream preferably consists of thermochemical ethanol or thermochemical methanol. Suitable alcohols include primary and secondary alcohols, as well as tertiary and other alcohols such as polyhydric alcohols. While $C_1$–$C_{12}$ alcohols are desireable, $C_1$–$C_8$ alcohols are more preferred, and $C_1$–$C_5$ alcohols are most preferred.

The mixed alcohol component is preferably synthesized from a Syn-Gas process utilizing as feedstock crude oil, coal, urban and/or industrial waste, biomass, lignite, shale oil or any other substance that would meet economic, energy, security and environmental objectives. The alcohols can also be produced by blending. However, blending may be less desireable economically as well as causing solubility and fungibility problems. In such a blending alternative the preferred alcohols will be $C_1$–$C_8$, and more preferably $C_1$–$C_4$. It may also be beneficial to include limited amounts of polyhydric alcohols in the mixed alcohol composition.

It is important to the performance of the invention that a continuous series of alcohols be used so as to ensure a smooth distillation curve either neat or in a mixture. Alcohol mixtures which lack one or more components in a range are less likely to provide the result desired, which is to produce a fuel or fuel blending agent which allows the mixed ether component to be used without having to modify current carburation systems, without having a detrimental effect on cold starting performance and other performance characteristics. It is believed that these objectives can be accomplished with a mixed ether gasoline component which, when mixed with gasoline, exhibits similar distillation characteristics compared to the unblended gasoline.

Experimental

Examples 1–5 demonstrate production processes and performance results for single boiling point ether gasoline components (examples 1 and 2, prior art) compared to multiple boiling point ether gasoline components (examples 3–5), i.e., preferred embodiments of the present invention.

The following experimental examples yielded data which is compared by way of 5 analytical tables. The tables include comparisons of distillation characteristics (ASTM D86 METHOD), analytical distillation deviation coefficients (by percentage), volatility and driveability factors, distillation temperature deviation factors, vapor pressure analyses: Reid Vapor Pressure (ASTM D 323), and octane levels.

In examples 1–5, ether-gasoline blends were made, each blend containing 15% (v/v) of a different ether containing blending agent. Each ether-gasoline blend was then distilled. The percent distilled (v/v) was observed and recorded as a function of temperature (shown in degrees Fahrenheit) throughout the distillation procedure.

The data was plotted with the % distilled (v/v) as the abscissa and the temperature as the ordinate, as shown in FIGS. 1–4. The plotted points were connected to form a distillation curve (hereafter "D-86 curve"). Although actual D-86 curves are only shown in FIGS. 1–4 for four ether components, the D-86 curve for each ether-gasoline blend was compared to the D-86 curve for unblended UNOCAL 89 base gasoline. These results are reported numerically in Tables 1–5. The objective is for the ether-gasoline blend' D-86 curve to be as close to the unblended gas' D-86 curve as possible, showing that the ether-gasoline blend will produce the desired performance characteristics in a motor which is designed to run on the unblended gasoline or equivalents.

EXAMPLE 1

In example 1, single boiling point alkyl t-alkyl ethers using $C_1$ to $C_8$ alcohols were reacted with isobutylene and compared. All oxygenated samples were blends in which the oxygenate accounted for 15.0% of the fuel. The 85.0% portion of the fuel consists of a clear gasoline typical of the UNOCAL unleaded grade with an AKI of about 89. Distillation, driveability, volatility and octane characteristics were determined for each blend. The results are reported in Table 1.

TABLE 1

|  | Unocal89 Run #1 | #601 MTBE | #602 ETBE | #603 n-$C_3$ TBE | #604 i-$C_3$ TBE | #605 n-$C_4$ TBE | #606 i-$C_4$ TBE |
| --- | --- | --- | --- | --- | --- | --- | --- |
| Initial Boiling Point (IBP) | 84 | 82 | 86 | 88 | 94 | 86 | 88 |
| T 10 | 112 | 114 | 114 | 122 | 119 | 128 | 132 |
| T 30 | 154 | 142 | 154 | 164 | 149 | 172 | 174 |
| Mid-Point T 50 | 200 | 178 | 186 | 208 | 192 | 222 | 219 |
| T 90 | 339 | 330 | 336 | 336 | 310 | 324 | 334 |
| Final Boiling Point (FBP) | 396 | 396 | 391 | 389 | 376 | 378 | 393 |
| % IBP Deviation v/s Run 1 | — | −2.3809 | +2.3809 | +4.7619 | +11.9048 | +2.3809 | +4.7619 |
| T 10 Deviation v/s Run 1 | — | +1.7857 | +1.7857 | +8.9286 | +6.2500 | +14.2857 | +17.8571 |
| T 30 Deviation v/s Run 1 | — | −7.7922 | =0.0000 | +6.4935 | −3.2467 | +11.6883 | +12.9870 |
| T 50 Deviation v/s Run 1 | — | −11.0000 | −7.0000 | +4.0000 | −4.0000 | +11.0000 | +9.5000 |
| T 90 Deviation v/s Run 1 | — | −2.6548 | −0.8850 | −0.8850 | −8.5546 | −4.4248 | −1.4750 |
| FBP Deviation v/s Run 1 | — | =0.0000 | −1.2626 | −1.7677 | −5.0505 | −4.5455 | −0.7576 |
| Driveability Index-DI | 426 | 400 | 411 | 437 | 407 | 448 | 452 |
| DTDF |  | 581 | 242 | 508 | 551 | 1035 | 1045 |
| RVP-Oxygenate | — | 8.05 | 4.30 | 2.00 | 3.00 | 0.90 | 1.55 |
| Research Octane #: RON | 94 | 97.4 | 97.4 | 96.5 | 97.1 | 93.6 | 95.6 |
| Motor Octane #: MON | 84.2 | 87.0 | 87.0 | 85.4 | 86.9 | 82.7 | 84.8 |
| AKI: (R + M)/2 | 89.1 | 92.2 | 92.2 | 91.0 | 92.0 | 88.2 | 90.2 |
| % RON Deviation | — | +3.6 | +3.6 | +2.7 | +3.3 | −0.4 | +1.7 |
| MON Deviation | — | +3.3 | +3.3 | +1.4 | +3.2 | −1.8 | +0.7 |
| AKI Deviation | — | +3.5 | +3.5 | +2.1 | +3.3 | −1.0 | +1.2 |

TABLE 1-continued

| | | | | | | | |
|---|---|---|---|---|---|---|---|
| Blending Research Octane Value (BROV) | 94.0 | 116.7 | 116.7 | 110.7 | 114.7 | 91.3 | 104.7 |
| Blending Motor Octane Value (BMOV) | 84.2 | 102.9 | 102.9 | 92.2 | 102.2 | 74.2 | 88.2 |
| BROV-BMOV Sensitivity | 9.8 | 13.8 | 13.8 | 18.5 | 12.5 | 17.1 | 16.5 |

| | #607<br>Sec-$C_4$<br>TBE | #608<br>n-$C_5$<br>TBE | #609<br>n-$C_6$<br>TBE | #617<br>n-$C_7$<br>TBE | #610<br>n-$C_8$<br>TBE |
|---|---|---|---|---|---|
| Initial Boiling Point (IBP) | 86 | 88 | 86 | 97 | 87 |
| T 10 | 112 | 122 | 122 | 132 | 127 |
| T 30 | 154 | 172 | 173 | 180 | 185 |
| Mid-Point T 50 | 204 | 230 | 234 | 242 | 252 |
| T 90 | 306 | 324 | 340 | 365 | 405 |
| Final Boiling Point (FBP) | 364 | 364 | 366 | 387 | 416 |
| % IBP Deviation v/s Run 1 | +2.3809 | +4.7619 | +2.3809 | +15.4762 | +3.5714 |
| T 10 Deviation v/s Run 1 | =0.0000 | +8.9286 | +8.9286 | +17.8571 | +13.3929 |
| T 30 Deviation v/s Run 1 | =0.0000 | +11.6883 | +12.3377 | +16.8831 | +20.1299 |
| T 50 Deviation v/s Run 1 | +2.0000 | +15.0000 | +17.0000 | +21.0000 | +26.0000 |
| T 90 Deviation v/s Run 1 | −9.7345 | −4.4248 | +0.2950 | +7.6696 | +19.4690 |
| FBP Deviation v/s Run 1 | −8.0808 | −8.0808 | −7.5758 | −2.2727 | +5.0505 |
| Driveability Index-DI | 413 | 453 | 465 | 491 | 518 |
| DTDF | 293 | 1001 | 964 | 1586 | 1975 |
| RVP-Oxygenate | 1.30 | 0.75 | 0.40 | 0.55 | 0.50 |
| Research Octane #: RON | 96.0 | 90.3 | 88.7 | 86.0 | 85.0 |
| Motor Octane #: MON | 86.2 | 80.5 | 79.7 | 78.4 | 77.2 |
| AKI: (R + M)/2 | 91.1 | 85.4 | 84.2 | 82.2 | 81.1 |
| % RON Deviation | +2.1 | −3.9 | −5.6 | −8.5 | −9.6 |
| MON Deviation | +2.4 | −4.4 | −5.3 | −6.9 | −8.3 |
| AKI Deviation | +2.2 | −4.2 | −5.5 | −7.7 | −9.0 |
| Blending Research Octane Value (BROV) | 107.3 | 69.3 | 58.7 | 40.7 | 34.0 |
| Blending Motor Octane Value (BMOV) | 97.5 | 59.5 | 54.2 | 45.5 | 37.5 |
| BROV-BMOV Sensitivity | 9.8 | 9.8 | 4.5 | −4.8 | −3.5 |

All samples evaluated within Table 1 show higher initial boiling points (IBP) and T10 evaporations relative to the UNOCAL 89, with the sole exception of the methyl tertiary-butyl ether (MTBE) blend, for which the initial boiling point dropped by about a 2.4% negative deviation. However, the direction of the deviation percentage for NTBE was reversed by T10 to a positive deviation of about 1.8%.

Two fuels, the MTBE Sample #601 and the isopropyl tertiary-butyl ether fuel blend sample #604 showed a drop at the T30 level.

MTBE, ethyl t-butyl ether (ETBE) and sample #604 showed a significant drop at T50 by 11, 7 and 4%, respectively.

All blends having $C_1$ to $C_5$ etherified fuel components showed a drop at T90. For $C_6$ to $C_8$ etherified alcohol blends, increases from 0.3 to 19.5% were observed. The most significant T90 drops occurred with fuel blends of iso-propyl t-butyl ether and sec-butyl t-butyl ether, with 8.6 and 9.7% negative deviations, respectively.

We observed that all blends had a final boiling point (FBP) drop with the exception of sample #610: N-octyl t-butyl ether (N-$C_8$TBE).

All of the single boiling point alkyl t-alkyl ethers in Table 1, when blended into gasoline, showed substantial positive and/or negative deviations from the distillation curves generated for neat gas. In the particular blends observed within Table 1, the total deviations range from as low as 9.4% (ETBE: 2.4% positive and 7.0% negative) to as high as 26.0% for n-octyl t-butyl ether.

This tends to indicate that, when using oxygenates, the refiner and/or gasoline blender should expect that the fuel gasoline blends which employ single boiling point ethers such as those in Table 1, will exhibit significantly different distillation characteristics compared to unblended gasoline.

For purposes of comparing the distillation characteristics of various blends a Distillation Temperature Deviation Factor (DTDF) was calculated by summing the absolute values of the deviation at T10, T30, T50 and T90 and multiplying by 25, i.e., according to the formula:

$$DTDF = \sum_{i=10}^{i=90} |Ti| \times 25$$

Thus, a lower DTDF indicates less distillation deviation from the unblend gasoline. It is notable that the only blends which have DTDF's below 500 are blend #602 and blend #607. However, both of these blends are relatively octane poor.

The distillation results are consistent with the driveability index (DI) figures.

The initial DI confirms superior performance from the MTBE, iso-propyl TBE and sec-butyl TBE blends.

Referring to the volatility factors, the vapor pressures of all of these oxygenate blends do provide fuel blending assets. All of the blends yield lower vapor pressures than traditional Reid vapor pressure values. However, it is known that for alcohols such as methanol (MeOH=$CH_3OH$) and/or Ethanol (EtOH=$C_2H_5OH$), the vapor pressure performance of a given oxygenate does not necessarily translate into beneficial features when blended with gasoline. Still, the RVP deviations do indicate superior performance for $C_2$, $C_4$, and $C_5$ to $C_8$ etherified blends.

Further, the octane values for, $C_1$ to $C_3$ etherified alcohols, and the i-$C_4$ and sec-$C_4$ etherified alcohols, when mixed with gasoline, were improved. Sec-$C_4$ TBE also reveals beneficial octane sensitivity qualities by reducing the gap that typically exists between MON and RON. The blends derived from etherified alcohols from $C_6$ to $C_8$ showed decreased octane values.

EXAMPLE 2

In example 2 single boiling point alkyl t-alkyl ethers using $C_1$ to $C_8$ alcohols were reacted with isoamylene and compared based on distillation, driveability, volatility and octane characteristics. All oxygenated samples were blends in which the oxygenate accounted for 15.0% of the fuel. The 85.0% portion of the fuel consisted of a clear gasoline typical of the UNOCAL unleaded grade with an AKI of about 89. The test results are reported in Table 2.

smallest DTDF was observed for Sample #618, i.e., 622. The largest DTDF was observed with the blend #625, i.e., DTDF=1569.

Figure 1:
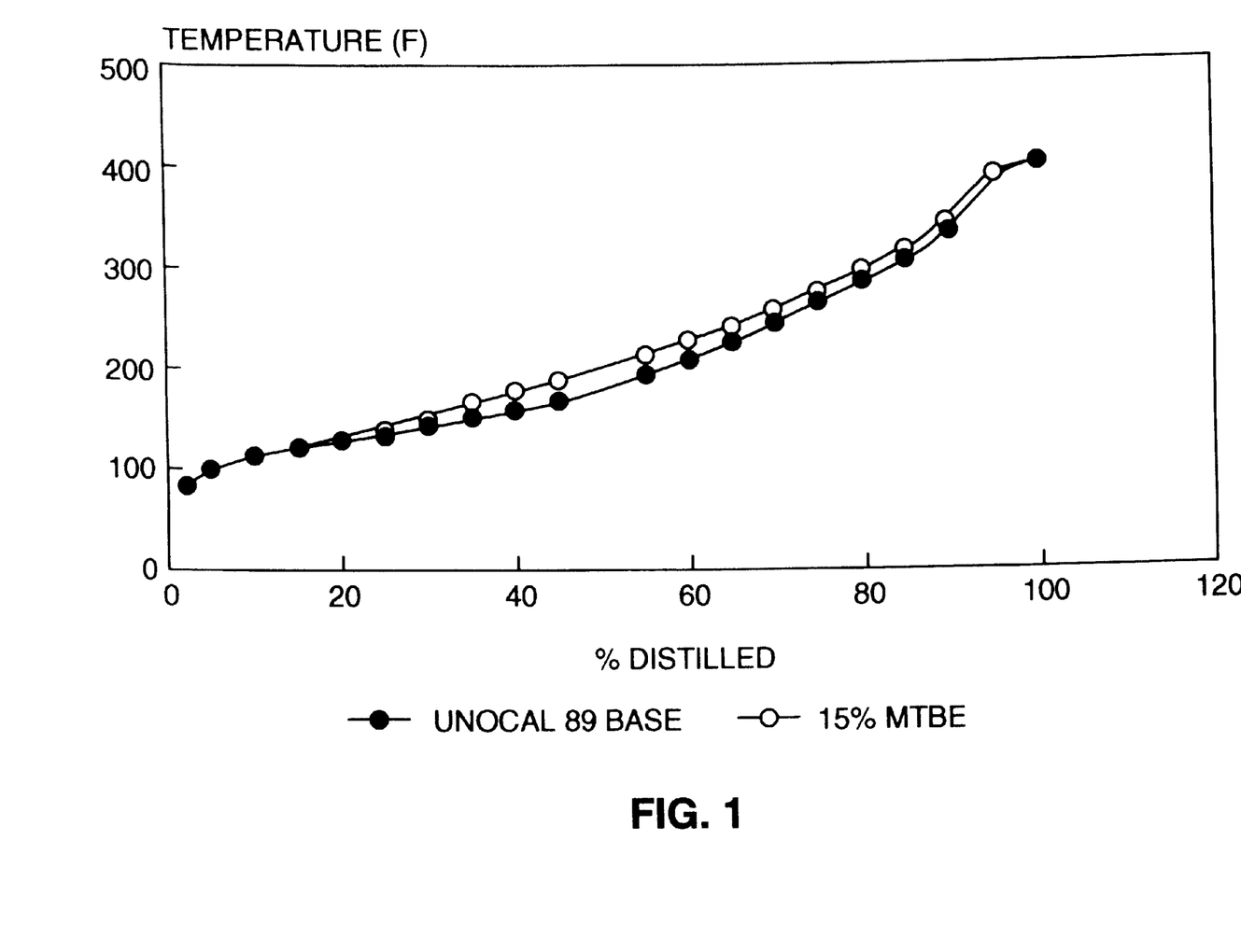
FIGS. 1, 2 and 3 are is a graphic plots of D-86 curves comparing the distillation characteristics of unmixed gasoline to gasoline blend that holds 15% v/v of a single boiling point ether component (MTBE, ETBE and TAME respectively, three commercially available ether products).
Figure 2:
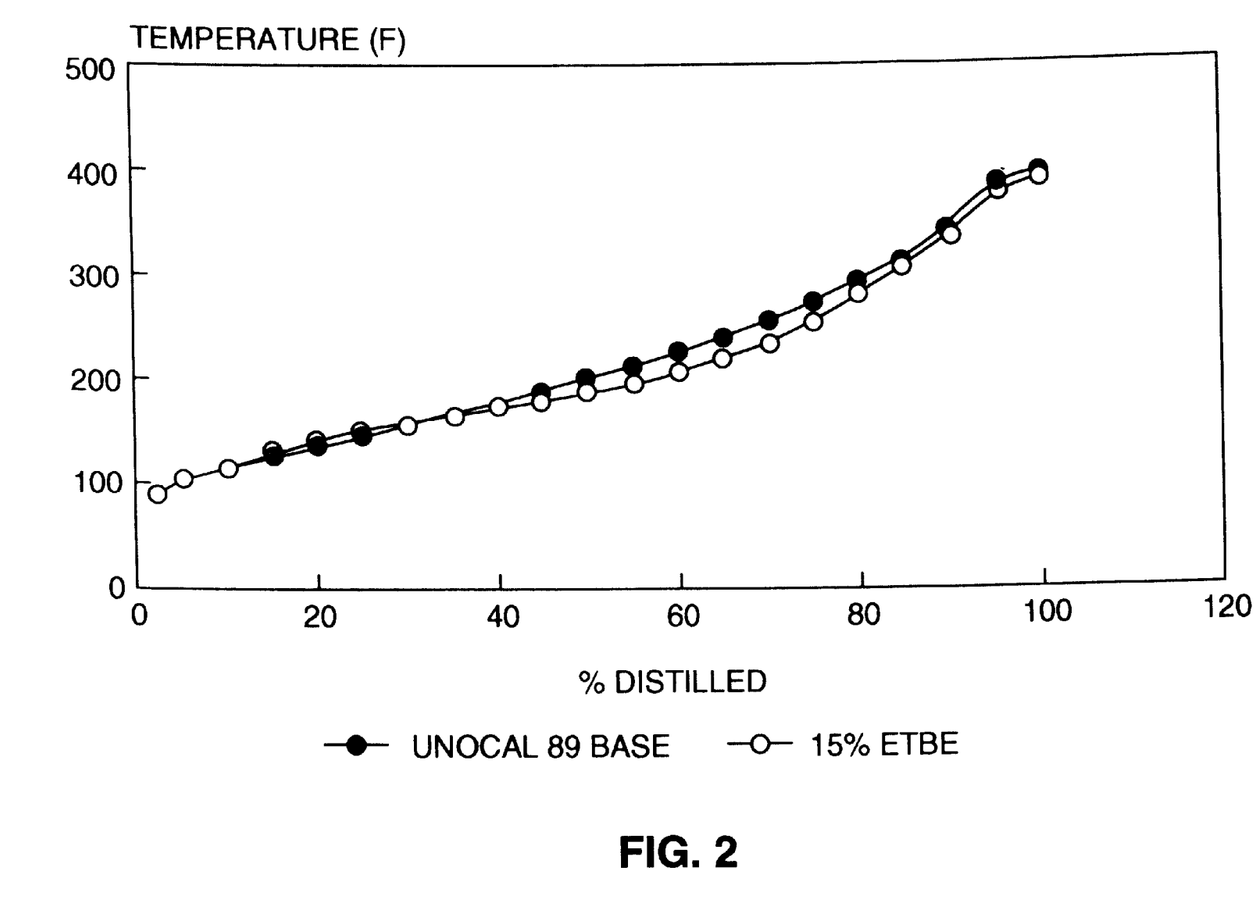
Figure 3:
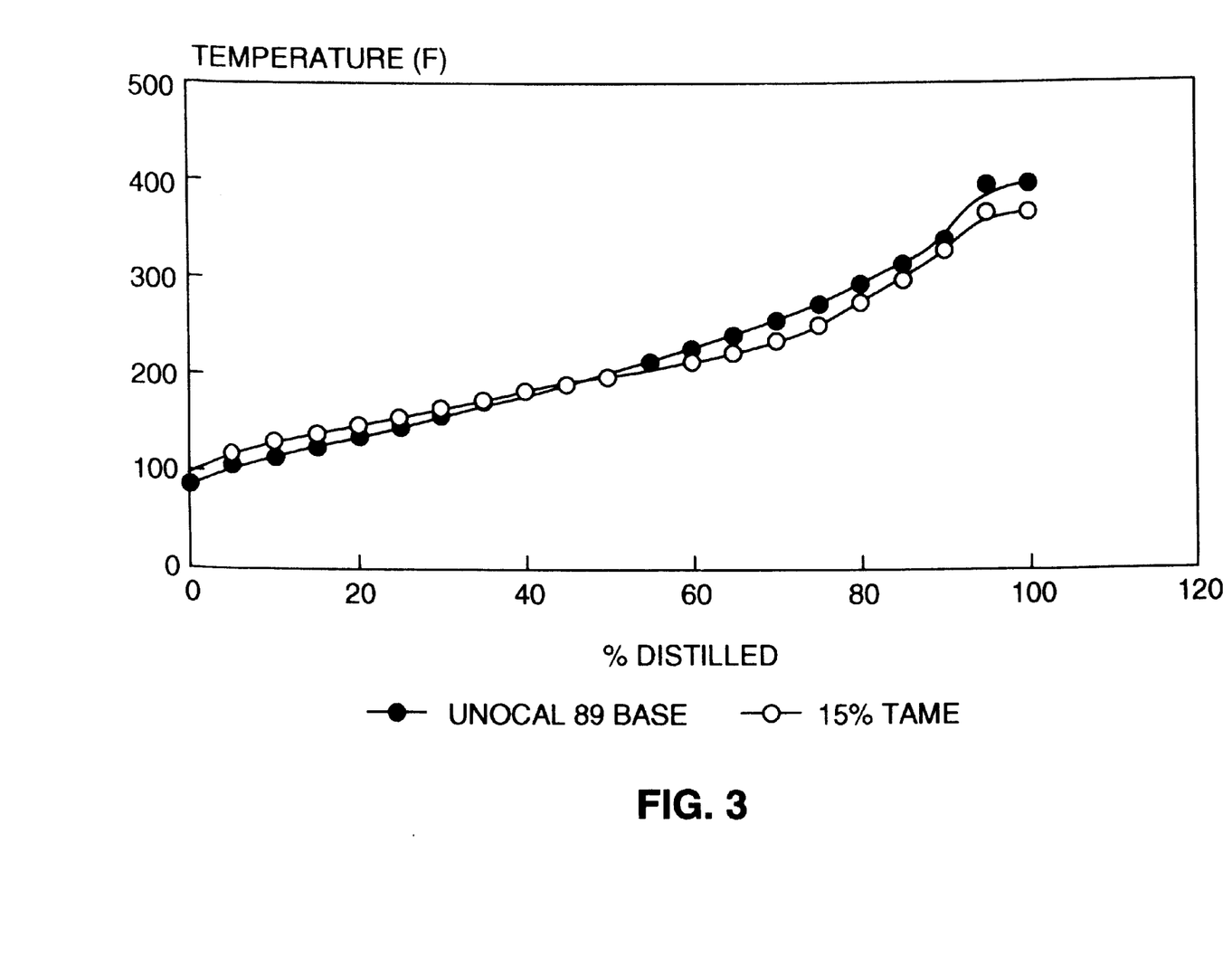
Figure 4:
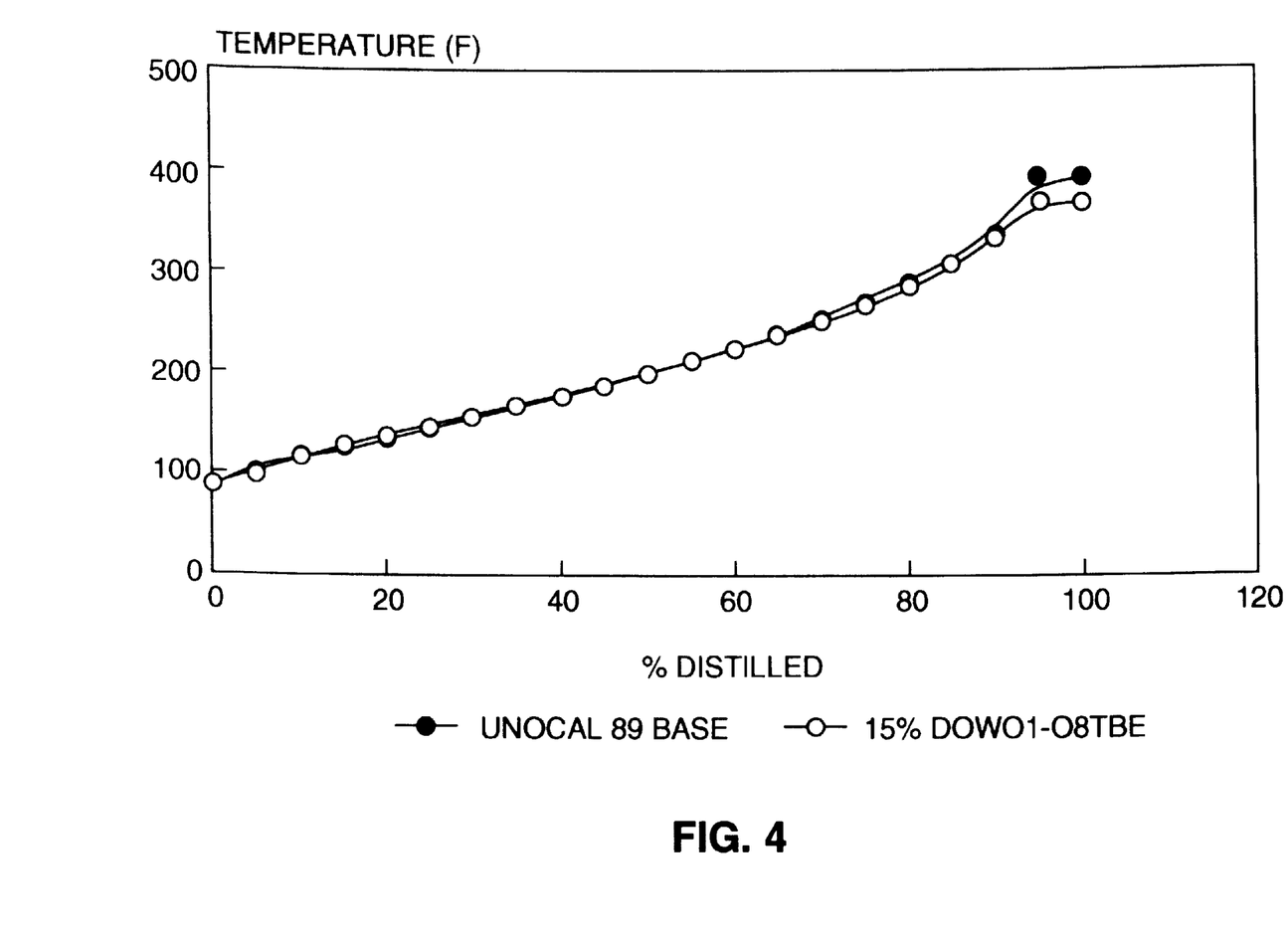
FIG. 4 is a graphic plot of D-86 curves comparing the distillation characteristics of unmixed gasoline to a gasoline blend that contains 15% v/v of a multiple boiling point ($C_1$–$C_8$) ether component according to an embodiment of the present invention.

The distillation results for blend #621, when graphically plotted against the distillation curve for neat gas, yielded a plot substantially as shown in FIG. 1. As shown in the graph, the deviation territory between the two curves is substantial.

In conclusion, the distillation data in Table 2 indicates that blends made with single boiling point ethers are not likely to exhibit similar motor fuel performance characteristics compared to neat gas.

Only the Sample #618: TAME showed an improvement in its DI index.

In terms of vapor pressure the overall results of Table 2 confirmed a greater susceptibility of the gasoline compo-

TABLE 2

| | Unocal89 Run #1 | #618 TAME | #619 ETAE | #620 n-$C_3$ TAE | #621 n-$C_4$ TAE | #622 n-$C_5$ TAE | #623 n-$C_6$ TAE | #624 n-$C_7$ TAE | #625 n-$C_8$ TAE |
|---|---|---|---|---|---|---|---|---|---|
| Initial Boiling Point (IBP) | 84 | 97 | 98 | 98 | 97 | 85 | 87 | 90 | 88 |
| T 10 | 112 | 128 | 134 | 132 | 134 | 127 | 123 | 124 | 124 |
| T 30 | 154 | 163 | 174 | 164 | 177 | 175 | 171 | 170 | 170 |
| T 50 | 200 | 197 | 212 | 210 | 229 | 231 | 232 | 230 | 232 |
| T 90 | 339 | 328 | 329 | 325 | 327 | 338 | 355 | 394 | 426 |
| Final Boiling Point (FBP) | 396 | 367 | 370 | 375 | 372 | 368 | 386 | 408 | 438 |
| % IBP Deviation v/s Run 1 | — | +15.4762 | +16.6666 | +16.6666 | +15.4619 | +1.1905 | +3.5714 | +7.1428 | +4.7619 |
| T 10 Deviation v/s Run 1 | — | +14.2857 | +19.6428 | +17.8571 | +19.6428 | +13.3928 | +9.8214 | +10.7143 | +10.7143 |
| T 30 Deviation v/s Run 1 | — | +5.8441 | +12.9870 | +6.4935 | +14.9350 | +13.6363 | +11.0390 | +10.3896 | +10.3896 |
| T 50 Deviation v/s Run 1 | — | −1.5000 | +6.0000 | +5.0000 | +14.5000 | +15.5000 | +16.0000 | +15.0000 | +16.0000 |
| T 90 Deviation v/s Run 1 | — | −3.2448 | −2.9498 | −4.1298 | −3.5398 | −0.2950 | +4.7198 | +16.2242 | +25.6637 |
| FBP Deviation v/s Run 1 | — | −7.3232 | −6.5656 | −5.3030 | −6.0606 | −7.0707 | −2.5252 | +3.0303 | +10.6061 |
| Driveability Index-DI | 426 | 425 | 444 | 439 | 460 | 464 | 471 | 489 | 701 |
| DTDF | | 622 | 1039 | 837 | 1315 | 1071 | 1040 | 1308 | 1569 |
| RVP-Oxygenate | — | 2.90 | 1.90 | 0.90 | 0.60 | 0.55 | 0.70 | 0.50 | 0.45 |
| Research Octane #: RON | 94 | 96.7 | 96.7 | 96.2 | 92.0 | 89.5 | 90.0 | 85.0 | 83.6 |
| Motor Octane #: MON | 84.2 | 86.0 | 86.5 | 85.4 | 83.5 | 80.1 | 80.1 | 77.9 | 76.8 |
| AKI: (R + M)/2 | 89.1 | 91.4 | 91.6 | 90.8 | 87.5 | 84.8 | 85.0 | 81.4 | 80.2 |
| % RON Deviation | — | +2.9 | +2.9 | +2.3 | −2.0 | −4.8 | −4.3 | −9.6 | −11.1 |
| MON Deviation | — | +2.1 | +2.7 | +1.4 | −0.8 | −4.9 | −4.9 | −7.5 | −8.8 |
| AKI Deviation | — | +2.6 | +2.8 | +1.9 | −1.8 | −4.8 | −4.6 | −8.6 | −10.0 |
| Blending Research Octane Value (BROV) | 94.0 | 112.0 | 112.0 | 108.7 | 80.7 | 64.0 | 67.3 | 34.0 | 24.7 |
| Blending Motor Octane Value (BMOV) | 84.2 | 96.2 | 99.5 | 92.2 | 79.5 | 56.9 | 56.9 | 42.2 | 34.9 |
| BROV-BMOV Sensitivity | 9.8 | 15.8 | 12.5 | 16.5 | 1.2 | 7.1 | 10.4 | −8.2 | −10.2 |

As shown in Table 2, it was observed that all blends, from IBP to T30 distillation points revealed higher temperature fractions than the neat UNOCAL gasoline. Further, the deviations were more substantial than those observed with the blends in Table 1, as reflected by the exceedingly high DTDF values. Only TAME dropped by T50 (mid-point), and only by as little as 1.5% negative deviation.

At T90, negative deviations were observed for blends including single individual alkyl t-alkyl ethers made from alcohols ranging from $C_1$ to $C_5$. Final boiling points gave negative deviations of up to 2.5% for sample #623 (N-$C_6$ TAE). The largest deviations at T90 were observed with samples #620 and #621: n-propyl and n-butyl t-amyl ether fuel blends.

Similar to the blends of Table 1, the single boiling point alkyl t-amyl ethers, when blended with gasoline, exhibited substantial positive and/or negative deviations from the distillation curves of the base gasoline alone. This result is reflected by the high DTDF values.

In general, the DTDF's increased significantly with the blends of Table 2 compared to the blends of Table 1. The nents to the oxygenates. However, the results are inconclusive. This volatility data is not sufficient to counter-balance the poor distillation performance which the Table 2 blends exhibited.

$C_1$ to $C_3$ etherifications showed octane improvements. N-butyl, n-heptyl, and n-octyl t-amyl ether gasoline blends showed octane sensitivity improvement characteristics. The best AKI data was observed with Sample #619:ETAE. It was also noted that octyl t-amyl ether yielded an 10.0% AKI negative deviation.

EXAMPLE 3

In example 3, mixed boiling point ethers (MBPE) of the present invention were compared. Alkyl t-alkyl ethers which were made from multiple boiling point alcohol blends including $C_1$ to $C_8$ alkanols and higher were used. For example, thermochemical methanol: a $C_{1-8}$ alcohol chain with a predominance of methanol +/−70% $CH_3OH$ or thermochemical ethanol: a $C_{1-8}$ alcohol chain with a predominance of $C_2$ and $C_3$ alcohols were used to make several of the MBPE samples tested. The ether samples were produced by reacting the alcohol blends with isobutylene and/or isoamylene.

Either reactant may be in molar excess to influence the complete conversion of the other reactant. Because etherification is an incomplete reaction the etherification comprises an unreacted stream of alcohol and liquid and/or gaseous oil derived hydrocarbons. While equimolar quantities of alcohol and iso-olefin are preferred, an excess between 2 and 200% of either component can be passed to the etherification reaction unit. Advantageously, the excess thermochemical methanol is about 30% or more when the hydrocarbon feedstream comprises significant quantities of iso-olefins, but equimolar quantities are preferred when the hydrocarbon feedstream consists primarily of $C_4$ hydrocarbons.

All oxygenated samples were blends, in which the oxygenate accounted for 15.0% of the fuel. The 85.0% portion of the fuel consisted of a clear gasoline typical of the UNOCAL unleaded grade with an AKI of about 89.

Tests were performed to compare the distillation, driveability, volatility and octane characteristics of the various MBPE blends. The results of these experiments are reported in Table 3.

tively small DTDF observed for a MBPE component compared to a single boiling point ether component, as shown in FIG. 1.

The following conclusions can be drawn for samples #614, and 626 to 630. First, by average, the blends of Table 3 show lower DTDF's compared to the blends of Tables 1 and 2. Second, in the first half of the ASTM-D86 distillation curves, the positive deviations range from as low as 0.9% to as high as 13.4%. The highest negative deviation was 5.8%. Third, the lowest DTDF was observed for thermochemical ethanol etherified blends. Fourth, in the second half of the distillation curves the distillation deviation percentages were mostly negative.

The data indicates that for gasoline as a hydrocarbon structure with multiple boiling point character, the most advantageous way to blend oxygen within its boiling range is to supplement and/or substitute some or more of its components with chemical structures of similar (multiple boiling point) character.

Overall, the blends of Table 3 are more suitable than the blends of Tables 1 and 2, as motor fuel substitutes. The data

TABLE 3

|  | UNOCAL89 Run #1 | $M-C_{1-4}$ TBE #611 | Thermo- MeOH TBE #614 | Thermo- MeOH TAE #626 | Thermo- MeOH TBE/TAE #627 | Thermo- EtOH TBE #628 | Thermo- EtOH TAE #629 | Thermo- EtOH TBE/TAE #630 |
|---|---|---|---|---|---|---|---|---|
| Initial Boiling Point (IBP) | 84 | 92 | 88 | 88 | 89 | 86 | 87 | 90 |
| T 10 | 112 | 125 | 113 | 124 | 122 | 116 | 124 | 127 |
| T 30 | 154 | 166 | 145 | 166 | 156 | 156 | 167 | 165 |
| Mid-Point T 50 | 200 | 209 | 184 | 204 | 196 | 200 | 210 | 208 |
| T 90 | 339 | 331 | 328 | 330 | 334 | 336 | 334 | 331 |
| Final Boiling Point (FBP) | 396 | 383 | 380 | 376 | 372 | 372 | 379 | 381 |
| % IBP Deviation v/s Run 1 | — | +9.5238 | +4.7619 | +4.7619 | +5.9524 | +2.3810 | +3.5714 | +7.1428 |
| T 10 Deviation v/s Run 1 | — | +11.6071 | +0.8928 | +10.7143 | +8.9286 | +3.5714 | +10.7143 | +13.3929 |
| T 30 Deviation v/s Run 1 | — | +7.7922 | −5.8441 | +7.7922 | +1.2987 | +1.2987 | +8.4415 | +7.1428 |
| T 50 Deviation v/s Run 1 | — | +4.5000 | −8.0000 | +2.0000 | −2.0000 | =0.0000 | +5.0000 | +4.0000 |
| T 90 Deviation v/s Run 1 | — | −2.3599 | −3.2448 | −2.6548 | −1.4749 | −0.8850 | −1.4749 | −2.3599 |
| FBP Deviation v/s Run 1 | — | −3.2828 | −4.0404 | −5.0505 | −6.0606 | −6.0606 | −4.2929 | −3.7879 |
| Driveability Index-DI | 426 | 437 | 405 | 431 | 424 | 426 | 439 | 437 |
| DTDF |  | 656 | 450 | 579 | 343 | 144 | 641 | 673 |
| RVP-Oxygenate | — |  | 5.95 | 2.10 | 4.75 | 2.70 | 1.70 | 3.25 |
| Research Octane #: RON | 94 | 96.2 | 97.3 | 95.6 | 95.8 | 95.6 | 94.6 | 95.0 |
| Motor Octane #: MON | 84.2 | 84.9 | 86.5 | 86.2 | 86.1 | 85.7 | 85.5 | 85.6 |
| AKI: (R + M)/2 | 89.1 | 90.4 | 91.9 | 90.9 | 91.0 | 90.6 | 90.0 | 90.3 |
| % RON Deviation | — | +2.3 | +3.5 | +1.7 | +1.9 | +1.7 | +0.6 | +1.1 |
| MON Deviation | — | +0.8 | +2.7 | +2.4 | +2.3 | +1.8 | +1.5 | +1.7 |
| AKI Deviation | — | +1.5 | +3.1 | +1.1 | +2.1 | +1.7 | +1.0 | +1.4 |
| Blending Research Octane Value (BROV) | 94.0 | 108.7 | 116.0 | 104.7 | 106.0 | 104.7 | 98.0 | 100.7 |
| Blending Motor Octane Value (BMOV) | 84.2 | 88.9 | 99.5 | 97.5 | 96.9 | 94.2 | 92.9 | 93.5 |
| BROV-BMOV Sensitivity | 9.8 | 19.8 | 16.5 | 7.2 | 9.1 | 10.5 | 5.1 | 7.2 |

Table 3 shows a general increase of IBP's ranging from 2.4 to approximately 9.5%. The evaporation temperature increase continues for most of the blends at their T10 points, deviating as much as about 13.4%.

All T90's and FBP's showed negative deviations. Current trends in gasoline reformulation indicate a desire to drop distillation temperatures, primarily at T90. A lower T90 translates into decreased emissions. It has been suggested that, by pursuing the trend of formulating to decrease T90's, it would be possible to make a gasoline which would burn as clean as methanol.

The distillation data for sample blend #611 was plotted compared to the D-86 curve for neat gas. The resulting plot is substantially shown in FIG. 2 demonstrating the comparain Table 3 allows us to predict which types and mixtures of oxygenated components will be beneficial as gasoline admixtures.

The DI values confirm the beneficial distillation data. The vapor pressure data is inconclusive. The superiority of multiple boiling point etherified alcohol chains compared to single boiling point alkyl t-alkyl ethers or blends is confirmed by the Octane values. All samples showed an overall AKI gain of at least 1.0%, up to 3.1% positive deviations. All blends except for Sample #614 showed octane sensitivity improvement characteristics.

EXAMPLE 4

In example 4 an etherified blend was produced by first synthesizing a mixed boiling point ether component by reacting $C_{2-4}$ alcohols with isobutylene. The ether component was then blended with gasoline at approximately 15.0% (v/v). Tests were then performed to determine the distillation, driveability, volatility and octane characteristics of the blend. The data reported in Table 4 emphasizes the possible characteristics which are obtainable with a thermochemical ethanol derived ether.

TABLE 4

|  | | EXXON87 UNLEADED | #501 $C_{2-4}$TBE |
|---|---|---|---|
| Initial Boiling Point (IBP) | | 78 | 80 |
| | T10 | 108 | 106 |
| | T20 | 130 | 129 |
| | T30 | 152 | 147 |
| | T40 | 174 | 166 |
| MID POINT | T50 | 199 | 186 |
| | T60 | 224 | 209 |
| | T70 | 252 | 238 |

TABLE 4-continued

|  | EXXON87 UNLEADED | #501 $C_{2-4}$TBE |
|---|---|---|
| T80 | 289 | 275 |
| T90 | 343 | 334 |
| FINAL BOILING POINT (FBP) | 416 | 410 |
| % IBP-DEVIATION | — | −2.5641 |
| T10-DEVIATION | — | −1.8519 |
| T30-DEVIATION | — | −3.2895 |
| T50-DEVIATION | — | −6.5327 |
| T90-DEVIATION | — | −2.6239 |
| FBP-DEVIATION | — | −1.4423 |
| DRIVEABILITY INDEX-DI | 425 | 406 |
| DTDF | — | 357 |
| RVP | 13.0 | 12.25 |
| RESEARCH OCTANE #: RON | 92.0 | 95.6 |
| MOTOR OCTANE #: MON | 82.6 | 85.0 |
| AKI: (R + M)/2 | 87.3 | 90.3 |
| % RON DEVIATION | — | +3.9 |
| % MON DEVIATION | — | +2.9 |
| % AKI DEVIATION | — | +3.4 |
| Octane Blending Sensitivity (OBS) | 9.4 | 10.6 |

The results shown in Table 4 (Sample #501) confirm the advantageous distillation performances of MBPE suggested by the data in Table 3. The DTDF restricted to 357, a figure which is substantially lower than almost all of the DTDF values shown in Tables 1 and 2 for the single boiling point ether blends. The DI dropped by nearly 5% demonstrating improved driveability. Octane values confirm substantial AKI improvement. However, the octane sensitivity improvements were less significant than those observed with the thermochemical ethanol and methanol blends.

EXAMPLE 5

In example 5 distillation, vaporization and overall volatility values were observed for mixed ether blends made with a summer grade UNOCAL 89 gasoline. MIX 1 was a blend (v/v) of ⅓ MTBE, ⅓ isopropyl TBE and ⅓ sec-butyl TBE. MIX 2 was a blend (v/v) of 28.3% MTBE, 28.3% isopropyl TBE, 28.3% of sec-butyl TBE, 5% methanol, 5% isopropanol and 5% sec-butyl alcohol. The test results are reported in Table 5.

TABLE 5

|  | UNOCAL89 SUMMER GRADE | 85% U-89SG 15% MIX 1 | 85% U-89SG 15% MIX 2 | 37 |
|---|---|---|---|---|
| Initial Boiling Point (IBP) | 97 | 98 | 100 | 99 |
| T10 | 134 | 136 | 130 | 136 |
| T20 | 151 | 152 | 148 | 150 |
| T30 | 170 | 169 | 164 | 165 |
| T40 | 195 | 189 | 187 | 184 |
| MID POINT T50 | 221 | 212 | 210 | 209 |
| T60 | 249 | 235 | 235 | 236 |
| T70 | 277 | 262 | 262 | 266 |
| T80 | 306 | 296 | 294 | 301 |
| T90 | 342 | 338 | 334 | 342 |
| FINAL BOILING POINT (FBP) | 400 | 388 | 392 | 397 |
| % IBP-DEVIATION | — | +1.0309 | +3.0928 | +2.0619 |
| T10-DEVIATION | — | +1.4925 | −2.9851 | +1.4925 |
| T30-DEVIATION | — | −0.5882 | −3.5294 | −2.9412 |
| T50-DEVIATION | — | −4.0724 | −4.9774 | −5.4299 |
| T90-DEVIATION | — | −1.1696 | −2.3392 | =0.0000 |
| FBP-DEVIATION | — | −3.0000 | −2.0000 | −0.7500 |
| DRIVEABILITY INDEX-DI | 459 | 449 | 442 | 448 |
| DTDF | | 183 | 346 | 247 |

MIX 1 showed a low DTDF of 183. MIX 2 showed a DTDF of 346 with a 3.0% increase in the IBP and a 5.0% drop in the mid-point of the ASTM D86 distillation curve. All driveability indices and volatility factors confirmed the beneficial distillation results.

While the mixed ether gasoline components of MIX 1 and MIX 2 yield beneficial distillation and volatility characteristics, thus verifying the results obtained with the MBP blends of Table 3, those skilled in the art will appreciate the substantial processing advantages of employing a mixed boiling point ether gasoline component which is made from a mixed alcohol instead of merely blending single boiling point ethers. In the present invention a mixed boiling point ether is produced by reacting a single stream of mixed alcohols with an alkene stream, thus requiring less equipment, less energy, less catalysts and less operating expense compared to producing single boiling point ethers separately and then mixing.

In conclusion, and in view of the CAA, it is interesting to observe that thermochemical alcohol chains, when etherified, do provide nearly the same oxygen concentrations as single boiling point ethers but have overall superior volatility characteristics and better octane sensitivity blending performance.

The present invention is not limited to mixed boiling point ethers made from olefins. It is also advantageous to employ an alkene stream consisting of hydrocarbons having two or more double bonds such as dienes, trienes, etc. An important advantage of using a diene, for example isoprene, is that at least three ethers can be synthesized from a single alcohol structure, through the same type of ion exchange resin catalyst. Further research has indicated that, by using a diene for etherification, three or more ethers can be produced for each alcohol that is reacted.

Isoprene is the preferred diene because of its reactivity and overall possible influence it could have on fuel emissions. However, others, such as, for example, cyclopentadiene and chloroprene could be advantageously employed.

The figures shown in Table 6 stress that for the refiner, whatever the gasoline distillation curve will be for a given blend, the clean air components will blend compatibably to that blend, without detriment to the gasolines to which the oxygenated components are admixed.

Although the foregoing invention has been described in some detail by way of illustration and example for purposes of clarity and understanding, it will be apparent to those of ordinary skill in the art that certain changes and modifications may be made thereto without departing from the spirit or scope of the claims.

TABLE 6

| COMPONENT | % - ASTM D86 DEVIATIONS TERRITORY + | - | ABS. DEVIATIONS | BP |
|---|---|---|---|---|
| MTBE | 1.7857 | 11.0000 | 12.7857 | 82–396 |
| ETBE | 1.7857 | 7.0000 | 8.7857 | 86–391 |
| N-C3TBE | 8.9286 | 0.8850 | 9.8136 | 88–389 |
| I-C3TBE | 11.9048 | 8.5546 | 20.4594 | 94–376 |
| I-C4TBE | 17.8571 | 1.4750 | 19.3321 | 88–393 |
| S-C4TBE | 2.0000 | 9.7345 | 11.7345 | 86–364 |
| TAME | 14.2857 | 3.2448 | 17.5305 | 97–367 |
| ETAE | 19.6428 | 2.9498 | 22.5926 | 98–370 |
| N-C3TAE | 17.8571 | 4.1298 | 21.9869 | 98–375 |
| THERMO-C1-TBE | 0.8928 | 8.0000 | 8.8928 | 88–380 |
| THERMO-C1-TAE | 10.7143 | 2.6548 | 13.3691 | 88–376 |
| THERMO-C1-TBE/TAE | 8.9286 | 2.0000 | 10.9286 | 89–372 |
| THERMO-C2-TBE | 3.5714 | 0.8850 | 4.4564 | 86–372 |
| THERMO-C2-TAE | 10.7143 | 1.4749 | 12.1892 | 87–379 |
| THERMO-C2-TBE/TAE | 13.3929 | 2.3599 | 15.7528 | 90–381 |

GASOLINE UNLEADED 89: BP 84-396/400.
ALL BOILING RANGES ARE PROVIDED IBP TO FBP.

What is claimed is:

1. A method for producing a mixed ether and gasoline containing composition to form an oxygenated fuel mixture comprising the steps of reacting a mixture containing $C_1$–$C_8$ alcohols with an alkene, to form an alkyl-t-alkyl mixed ether composition; and mixing said ether composition with gasoline.

2. The method of claim 1 wherein said alcohol mixture is predominantly methanol and includes at least about 25% (v/v) alcohol having two or more carbons.

3. The method of claim 1 wherein said alcohol mixture is predominantly ethanol and isopropanol.

4. The method of claims 1 wherein said alcohol mixture includes methanol, ethanol, propanol and butanol and said alkene is isobutylene.

5. The method of claim 1 wherein said alcohol mixture includes methanol, ethanol, propanol and butanol and said alkene is isoamylene.

6. The method of claim 1 comprising the additional step of reacting a hydrocarbon containing source stream to produce said alcohol mixture.

7. The method of claim 1 wherein said ether composition is mixed in an amount sufficient to form a 15% (v/v) mixture based on said gasoline.

8. The method of claim 1 wherein said alcohol mixture further comprises water in an amount greater than 0.1% (v/v).

9. A composition comprising a mixture of 85% gasoline and 15% of an ether containing product, said ether containing product being formed by the steps of preparing a blend of $C_1$–$C_8$ alcohols and reacting said blend with isoamylene.

* * * * *